(12) United States Patent
Hanna

(10) Patent No.: US 7,510,541 B2
(45) Date of Patent: Mar. 31, 2009

(54) CLOSURE CAP FOR LACHRYMAL CANALICULUS

(75) Inventor: Khalil Hanna, 5 reu Cognacq Jay, Paris (FR) 75007

(73) Assignees: Khalil Hanna, Paris (FR), 50% Interest; Bruno Fayet, Paris (FR), 50% Interest ( * ) Notice: Subject to any disclaimer, the term of this patent is extended or adjusted under 35 U.S.C. 154(b) by 335 days.

(21) Appl. No.: 10/527,324

(22) PCT Filed: Sep. 5, 2003

(86) PCT No.: PCT/FR03/02656

§ 371 (c)(1),
(2), (4) Date: Mar. 10, 2005

(87) PCT Pub. No.: WO2004/024043

PCT Pub. Date: Mar. 25, 2004

(65) Prior Publication Data

US 2006/0122553 A1    Jun. 8, 2006

(30) Foreign Application Priority Data

Sep. 11, 2002    (FR)    .................................. 02 11227

(51) Int. Cl.
*A61B 17/00* (2006.01)
*A61M 5/00* (2006.01)

(52) U.S. Cl. ........................................... 604/9; 128/887

(58) Field of Classification Search .................... 604/8, 604/9, 264; 128/887; 606/109, 153
See application file for complete search history.

(56) References Cited

U.S. PATENT DOCUMENTS

| 4,959,048 | A |   | 9/1990 | Seder et al. |
| 5,318,513 | A | * | 6/1994 | Leib et al. ...................... 604/8 |
| 5,993,407 | A | * | 11/1999 | Moazed ......................... 604/8 |
| 6,238,363 | B1 | * | 5/2001 | Kurihashi ...................... 604/8 |
| 6,406,453 | B1 | * | 6/2002 | Goode et al. ................... 604/8 |
| 6,629,533 | B1 | * | 10/2003 | Webb et al. ................. 128/887 |
| 2003/0018291 | A1 | * | 1/2003 | Hill et al. ....................... 604/8 |

FOREIGN PATENT DOCUMENTS

EP    0445946 A1 *    2/1990
FR    2 747 033        10/1997

* cited by examiner

*Primary Examiner*—Leslie R Deak
(74) *Attorney, Agent, or Firm*—Young & Thompson

(57) ABSTRACT

A plug for the meatus of a lacrimal canaliculus, the plug including an elongate body (2, 12, 13) having a longitudinal axis (2a) and provided at one of its ends with a collar (1, 11) substantially perpendicular to the longitudinal axis, in which the elongate body (2, 12, 13) possesses a first portion (2, 12) adjacent to the collar (1, 11) of cross-section that is elliptical with a major axis, and a second portion (3, 4, 13) which extends the first portion (2) obliquely relative to its longitudinal axis (2a) in the plane of the above-mentioned major axis of the section of the first portion.

7 Claims, 2 Drawing Sheets

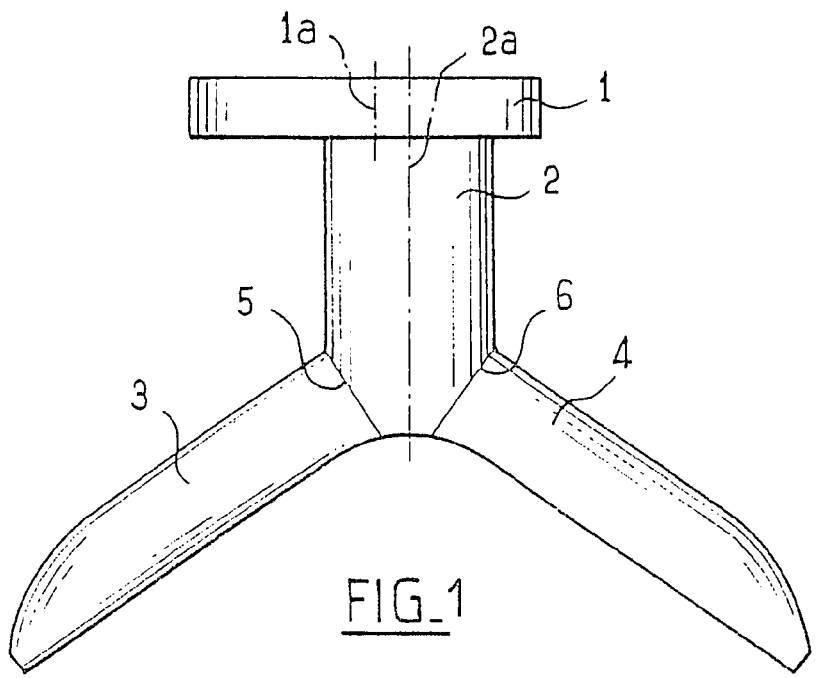
FIG_1
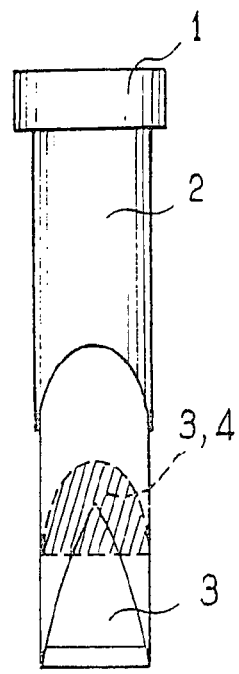
FIG_2
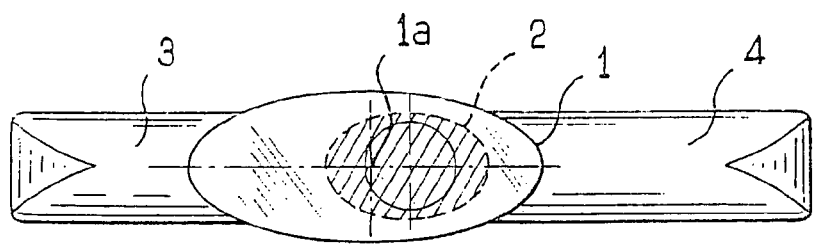
FIG_3
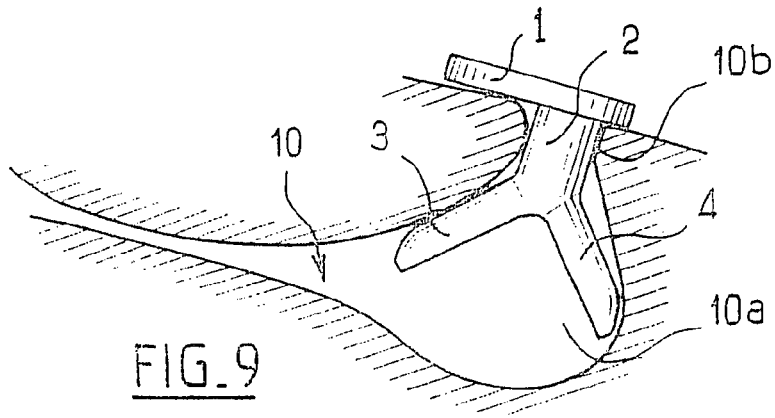
FIG_9
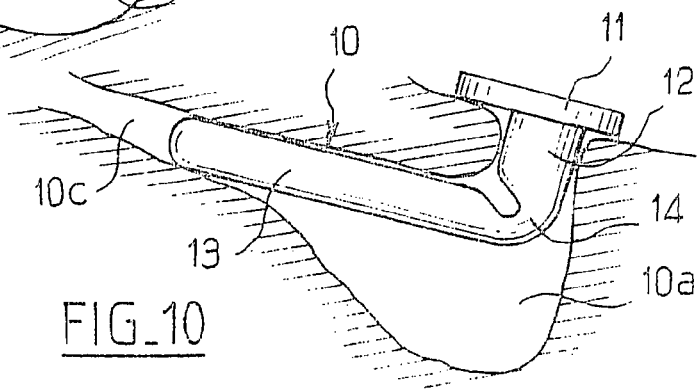
FIG_10

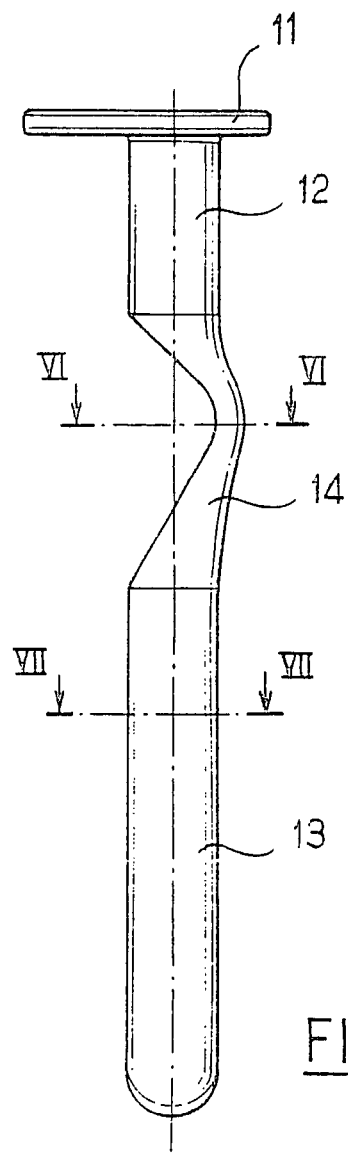
FIG_4
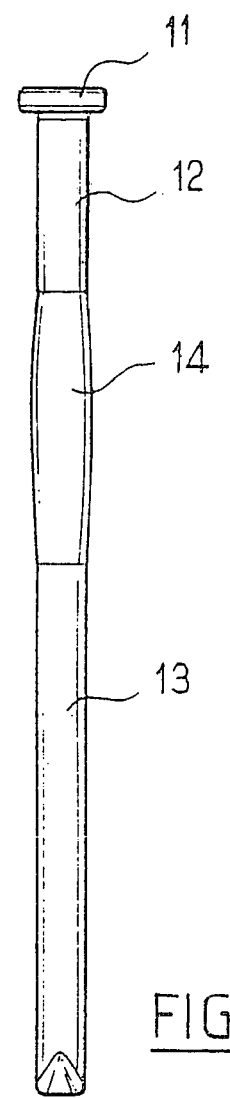
FIG_5
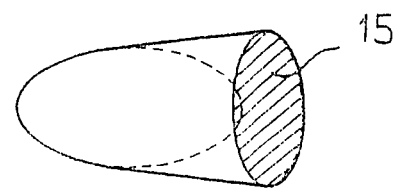
FIG_6
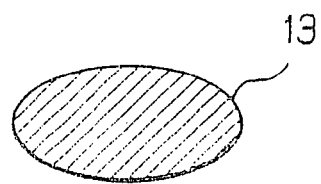
FIG_7
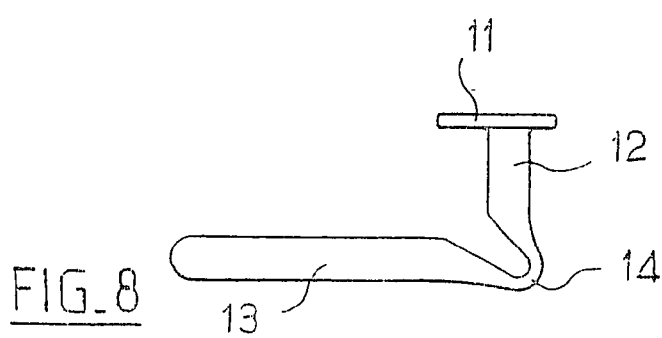
FIG_8

CLOSURE CAP FOR LACHRYMAL CANALICULUS

The present invention relates to a plug for closing the meatus of a lacrimal canaliculus to remedy in particular disorders known as "dry eye" which are due to insufficient secretion of lacrimal liquid.

BACKGROUND OF THE INVENTION

Numerous plugs are known for performing this function. Most of them are of a shape that is designed to prevent the plug from being expelled or from disappearing into the lacrimal canaliculus. For this purpose, practically all plugs have a top collar which is preferably inclined relative to the general axis of the plug in order to bear against the edges of the meatus and thus constitute means for preventing the plug disappearing into the canaliculus, and also an enlarged portion remote from the collar forming anti-expulsion means.

The drawbacks of known plugs lie in the fact that their shapes do not comply with the natural anatomic shapes of lacrimal canaliculi and constitute sources of trauma to tissues adjacent to such canaliculi.

OBJECTS AND SUMMARY OF THE INVENTION

The present invention seeks to remedy those drawbacks by means of a plug that can be put into place with as little trauma as possible for the tissues concerned, and also that it gives rise to as little as trauma as possible during long-term presence in the canaliculus that it is closing, while nevertheless ensuring that it is held effectively in the canaliculus.

To this end, the invention provides a plug for the meatus of a lacrimal canaliculus, the plug comprising an elongate body having a longitudinal axis and provided at one of its ends with a collar substantially perpendicular to said longitudinal axis, in which the elongate body possesses, adjacent to the collar, a first portion of cross-section that is elliptical with a major axis, and a second portion that extends the first portion obliquely relative to its longitudinal axis in the plane of the above-mentioned major axis of the section of the first portion.

The general shape of the plug is then closer to the anatomic shape of the lacrimal canaliculus with which it is to co-operate.

In a first embodiment, the second portion of the elongate body comprises two diverging branches, each of cross-section substantially equal to half the cross-section of the first portion.

This shape is well adapted to the morphology of the vertical initial portion of the lacrimal canaliculus to be closed which includes a kind of pocket that is relatively flat parallel to the skin of the subject.

In a second embodiment, the second portion of the elongate body is similar in section to the first portion and is connected to the first portion by a pseudo-hinge formed by a transition zone of cross-section that is narrow in the direction of the major axes of the above-mentioned ellipses. The length of the second portion is long so as to be received in the horizontal portion of the lacrimal canaliculus situated beyond the pocket in order to form a probe for treating the lacrimal canaliculus in which it is placed.

Preferably, in each of the above embodiments, the angle of the second portion relative to the first is maintained elastically, thus enabling the body to be straightened out when the plug is put into place in order to facilitate insertion thereof.

This elasticity is due to the material used, which is elastically deformable away from the shape that is imparted to it during manufacture (for example a biocompatible elastomer or a silicone).

BRIEF DESCRIPTION OF THE DRAWINGS

Other characteristics and advantages of the invention appear from the following description of embodiments given below as examples.

Reference is made to the accompanying drawings, in which:

FIG. 1 is a view of the outside of a plug of the invention in a first variant embodiment;

FIG. 2 is a side view of the outside of the plug;

FIG. 3 is a plan view of the plug;

FIG. 4 is a front view of a second variant embodiment of the plug of the invention;

FIG. 5 is a side view of this variant;

FIG. 6 is a section view on line VI-VI of FIG. 4;

FIG. 7 is a section view on line VII-VII of FIG. 4;

FIG. 8 is a view of the outside of the FIG. 4 plug in its angled state; and

FIGS. 9 and 10 show two variant embodiments of the plug of the invention put into place in the outlet of a lacrimal canaliculus.

MORE DETAILED DESCRIPTION

In FIGS. 1 to 3, the plug shown comprises a top collar 1 of elliptical shape having a segment 2 of an elongate body extending beneath it along a longitudinal axis 2a, the body being likewise elliptical in section with the major axis of the ellipse of the section coinciding with that of the collar 1, said segment 2 forming a first portion of the plug having connected thereto two branches 3 and 4 that diverge away from each other in a plane containing the major axes of the above-mentioned ellipses. The section of each branch 3, 4 is semi-elliptical with the major axis thereof likewise lying in said plane. It should be observed that the center 1a of the elliptical collar 1 does not coincide with the axis 2a, but is offset from said axis 2a along the major axis.

FIG. 9 shows this plug in place in the first section of a lacrimal canaliculus 10 which forms a sac 10a flaring from the meatus 10b through which the plug is inserted. In order to insert the plug, it is necessary to move its branches 3 and 4 towards each other by means of a suitable injector appliance (not shown) so that they occupy space that is no greater than or only slightly greater than the through orifice defined by the meatus 10b of the lacrimal canaliculus 10. On being moved towards each other, the branches 3 and 4 pivot relative to the segment 2 in transition zones 5 and 6 that form pseudo-hinges between the branches and the segments. Like the entire plug, these pseudo-hinges are elastic and tend to cause the branches 3 and 4 to diverge. With a plug made of suitable material, in particular a hydrophilic plastics material of known type, it is possible to prepare the plug by folding down the branches 3 and 4 about their hinges 4 and 5 so that they come into contact with each other, and then by dehydration causing the plug to retain this shape without it being necessary to apply any external stress. It is thus while it is in a shape that is substantially straight that the plug is inserted into the meatus 10b of the lacrimal canaliculus 10. Under the effect of the moisture that is to be found inside the canaliculus, the branches 3 and 4 then diverge progressively so as to reach the state shown in FIG. 9.

It should be observed that the sum of the sections of the branches 3 and 4 is substantially equal to the section of the segment 2. The oblong shapes of these segments match the naturally oblong shape of the meatus 10b.

The plug shown in FIGS. 4 to 8 and in FIG. 10 where it is shown implanted in the lacrimal canaliculus 10, is designed to act mainly as a probe for treating disorders of lacrimal canaliculi. Like the above-described plug, it comprises an elliptical top collar 11, a first elongate body portion 12 of elliptical section like the outline of the collar 11 and with a major axis oriented in the same direction, a second elongate body portion 13 identical to the portion 12 in section (which section is shown in FIG. 7), and a transition zone 14 which interconnects the first and second portions 12 and 13. The zone 14 is formed by a flattened portion of the plug body of section as shown at 15, such that the major axis of this section is perpendicular to the major axes of the elliptical sections 12 and 13, thereby constituting a preferred bending zone or pseudo-hinge between the portions 12 and 13 of the plug. The flattening defines the plane in which the plug can deform: this plane is the plane containing the major axes of the elliptical sections of the portions 12 and 13 and of the collar 11.

In FIGS. 4 and 5, the plug is shown straightened out, i.e. under the influence of external forces which may be constituted by the force of gravity if the zone 15 is very flexible, or by a dehydrated state of a hydrophilic material having shape memory in the rest state, i.e. under moist conditions that enable it to be hydrated as shown in FIG. 8.

It can be seen that the section of the plug all along its portions 12, 13, and 14 is substantially constant and matches the natural orifice defined by the meatus 10b of the lacrimal canaliculus 10. It will also be observed that when the portions 12 and 13 are in alignment, the section 14 constitutes a highly flexible zone enabling the plug to be inserted into the horizontal portion 10c of the lacrimal canaliculus 10 (see FIG. 10).

In a variant embodiment, when at rest, the plug may take up the shape shown in FIG. 8, and it needs to be straightened out elastically in order to be inserted into the lacrimal canaliculus. Once therein, it takes up the shape shown in FIG. 10.

It will have been observed that the second portion of the plug shown in FIGS. 4 to 8 is much longer than the second portion of the plug shown in FIGS. 1 to 3, i.e. the branches 3 and 4. FIGS. 9 and 10 show the different ways in which they are implanted, and thus the reason why the portion 13 of the second plug needs to be much longer than the branches 3 and 4 of the first plug.

The invention claimed is:

1. A plug for the meatus of a lacrimal canaliculus, the plug comprising:
    an elongate body having a longitudinal axis; and
    an elliptical collar with a major axis, provided at one end of said elongate body, said collar substantially perpendicular to said longitudinal axis, wherein,
    said elongate body has
    i) a first portion attached, at said one end, to said collar, and
    ii) a second portion made of two branches,
    said two branches each extend beyond said first portion in a direction away from said collar,
    said two branches are elastically connected to said first portion in order to be biased each branch against the other branch and to diverge elastically each branch from the other branch in a plane including the longitudinal axis and the major axis of the elliptical collar.

2. A plug according to claim 1, wherein said first portion is elliptical with an elliptical cross-section perpendicular to the longitudinal axis and the elliptical cross section having a major axis, and each of said two branches has a cross-section substantially equal to half of the elliptical cross-section of said first portion, said major axis being parallel to the major axis of the collar.

3. A plug according to claim 1, wherein the collar is offset relative to the longitudinal axis of the elongate body.

4. A plug for the meatus of a lacrimal canaliculus, the plug comprising:
    an elliptical elongate body extending along a longitudinal axis, an elliptical cross-section perpendicular to the longitudinal axis having a major axis;
    a collar provided at a first end of said elongate body, said collar substantially perpendicular to said longitudinal axis; and
    two branches elastically connected at a second end of said elongate body,
    said two branches each extending beyond said elongate body in a direction away from said collar,
    said two branches biased each branch against the other branch,
    said two branches diverging elastically, each branch from the other branch, in a plane including the longitudinal axis and the major axis of the elliptical cross-section of said elongate body,
    a sum of the cross-sections of said two branches is substantially equal to the elliptical cross-section of said elongate body, wherein,
    i) each of said two branches, at rest, are diverging and extend obliquely relative to said longitudinal axis away from said collar,
    ii) during insertion into the meatus said two branches are brought together under action of an injector appliance for locating the plug into the meatus, and
    iii) subsequent to insertion into the meatus, said two branches are diverging elastically each branch from the other branch.

5. A plug according to claim 4, wherein the collar is elliptical in outline with a major axis parallel to the major axis of the elongate body.

6. A plug according to claim 5, wherein the collar is offset relative to the longitudinal axis of the elongate body.

7. A plug according to claim 5, wherein each of said two branches having a cross-section substantially equal to half of the elliptical cross-section of said elongate body.

* * * * *